(12) United States Patent
Sugiyama et al.

(10) Patent No.: US 9,877,678 B2
(45) Date of Patent: Jan. 30, 2018

(54) VEHICLE SEAT

(71) Applicants: TS TECH CO., LTD., Asaka-shi, Saitama (JP); JOSHO GAKUEN EDUCATIONAL FOUNDATION, Osaka-shi, Osaka (JP); NIHON UNIVERSITY, Tokyo (JP)

(72) Inventors: Shinji Sugiyama, Tochigi (JP); Toyokazu Nakano, Tochigi (JP); Mieko Ohsuga, Osaka (JP); Ichiro Kageyama, Tokyo (JP); Yukiyo Kuriyagawa, Tokyo (JP); Shu Iida, Tokyo (JP)

(73) Assignees: TS Tech Co., Ltd., Saitama (JP); Josho Gakuen Educational Foundation, Osaka (JP); Nihon University, Tokyo (JP)

( * ) Notice: Subject to any disclaimer, the term of this patent is extended or adjusted under 35 U.S.C. 154(b) by 551 days.

(21) Appl. No.: 14/395,408

(22) PCT Filed: Apr. 18, 2013

(86) PCT No.: PCT/JP2013/061521
§ 371 (c)(1),
(2) Date: Oct. 17, 2014

(87) PCT Pub. No.: WO2013/157609
PCT Pub. Date: Oct. 24, 2013

(65) Prior Publication Data
US 2015/0061347 A1    Mar. 5, 2015

(30) Foreign Application Priority Data

Apr. 19, 2012 (JP) ................................. 2012-095789

(51) Int. Cl.
*A61B 5/18* (2006.01)
*A61B 5/113* (2006.01)
(Continued)

(52) U.S. Cl.
CPC .............. *A61B 5/18* (2013.01); *A61B 5/0053* (2013.01); *A61B 5/0816* (2013.01); *A61B 5/113* (2013.01);
(Continued)

(58) Field of Classification Search
CPC ....................................................... A61B 5/18
(Continued)

(56) References Cited

U.S. PATENT DOCUMENTS 8,478,486 B2 * 7/2013 Kato ...................... B60N 2/002
340/467
8,725,311 B1 * 5/2014 Breed .................... G08B 21/06
600/300

(Continued)

FOREIGN PATENT DOCUMENTS

EP      1 639 941 A1    3/2006
JP      2001-194218 A   7/2001
(Continued)

OTHER PUBLICATIONS

Extended European Search Report issued for EP 13779045.7 (dated May 28, 2015).
(Continued)

*Primary Examiner* — Gregory J Toatley
*Assistant Examiner* — Douglas Kay
(74) *Attorney, Agent, or Firm* — Drinker Biddle & Reath LLP

(57) ABSTRACT

A respiration signal of a seated person is detected with high accuracy by using a vehicle seat that includes a seat cushion; and a sensor detecting a pressure signal from a load applied
(Continued)

from a seated person. The sensor is provided to be along an edge of a contact portion between the seat cushion and buttocks of the seated person. The sensor transmits the detected pressure signal to an arithmetic operation device of the seated person. In a respiration measuring device, the arithmetic operation device computes the detected pressure signal detected by the sensor to obtain a respiration signal of the seated person.

9 Claims, 19 Drawing Sheets

(51) Int. Cl.
    *A61B 5/08*                  (2006.01)
    *B60N 2/00*                (2006.01)
    *A61B 5/00*                (2006.01)

(52) U.S. Cl.
    CPC .......... *A61B 5/6893* (2013.01); *A61B 5/7278* (2013.01); *B60N 2/002* (2013.01); *A61B 2562/0247* (2013.01); *A61B 2562/0261* (2013.01)

(58) Field of Classification Search
    USPC ........................................................ 702/127
    See application file for complete search history.

(56) References Cited

U.S. PATENT DOCUMENTS

| | | | | |
|---|---|---|---|---|
| 2004/0245036 | A1* | 12/2004 | Fujita | B60N 2/002 180/272 |
| 2007/0112283 | A1 | 5/2007 | Ando et al. | |
| 2008/0121511 | A1* | 5/2008 | Saitoh | B60N 2/002 200/85 A |
| 2009/0107258 | A1* | 4/2009 | Saitoh | B60N 2/002 73/862.046 |
| 2010/0018327 | A1 | 1/2010 | Kogure et al. | |
| 2011/0196243 | A1 | 8/2011 | Wu et al. | |
| 2012/0010514 | A1† | 1/2012 | Vrazic | |
| 2012/0016247 | A1 | 1/2012 | Vrazic | |
| 2012/0330113 | A1 | 12/2012 | Kogure | |
| 2013/0012837 | A1* | 1/2013 | Kogure | A61B 5/11 600/595 |

FOREIGN PATENT DOCUMENTS

| | | | |
|---|---|---|---|
| JP | 2005-342188 A | | 12/2005 |
| JP | 2005342188 A | † | 12/2005 |
| JP | 2007-261310 A | | 10/2007 |
| JP | 2011-156196 A | | 8/2011 |
| JP | 2011-156197 A | | 8/2011 |
| JP | 2011156197 A | † | 8/2011 |
| WO | WO 97/40748 A1 | | 11/1997 |
| WO | 2011/030491 A1 | | 3/2011 |
| WO | 2011096144 A1 | † | 8/2011 |
| WO | WO 2011/096144 A1 | | 8/2011 |
| WO | 2011/114819 A1 | | 9/2011 |
| WO | WO 2011/118280 A1 | | 9/2011 |

OTHER PUBLICATIONS

Examination Report issued for related application EP 13779045.7, dated Apr. 6, 2016, 5 pages.

\* cited by examiner
† cited by third party

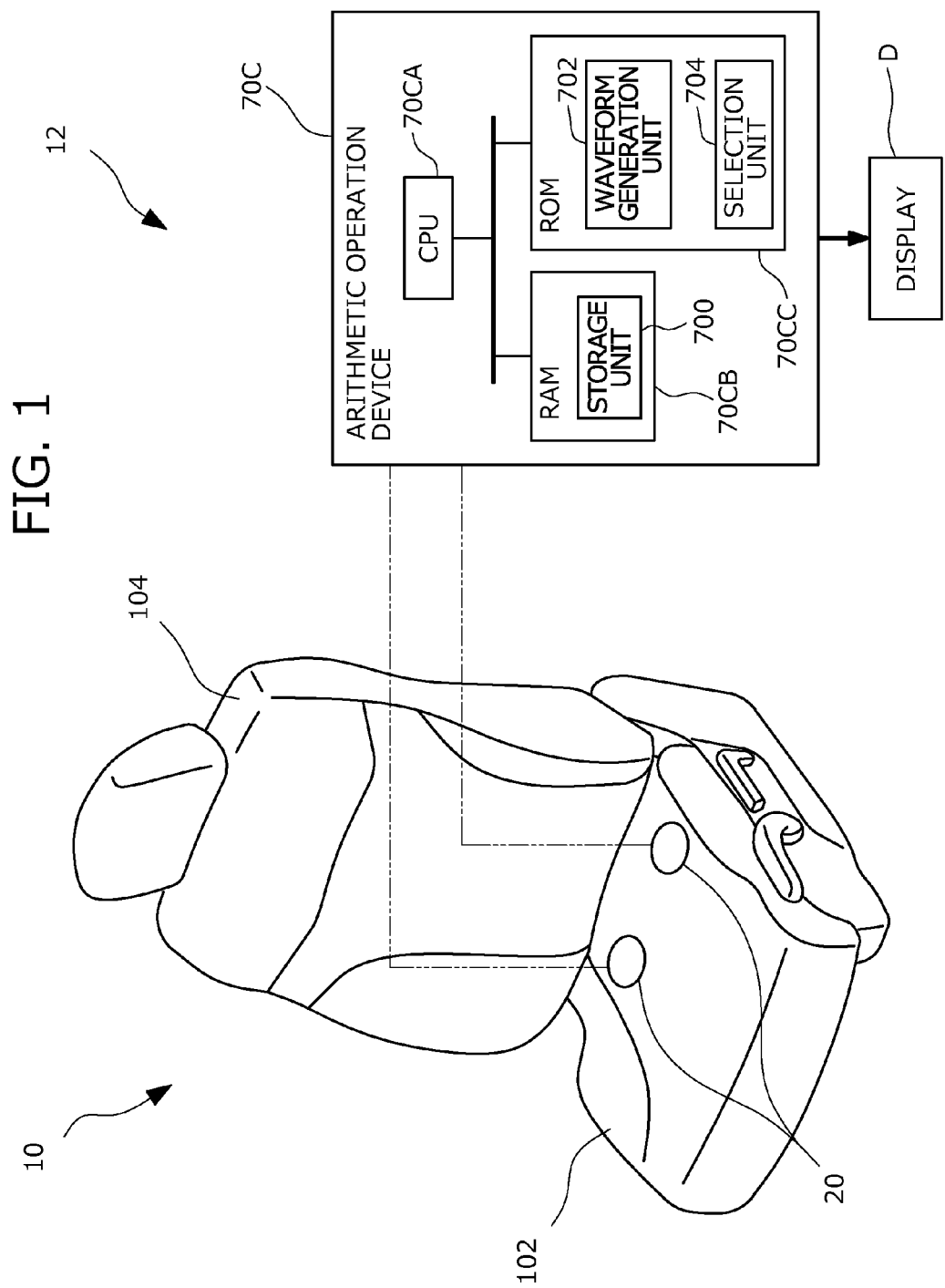

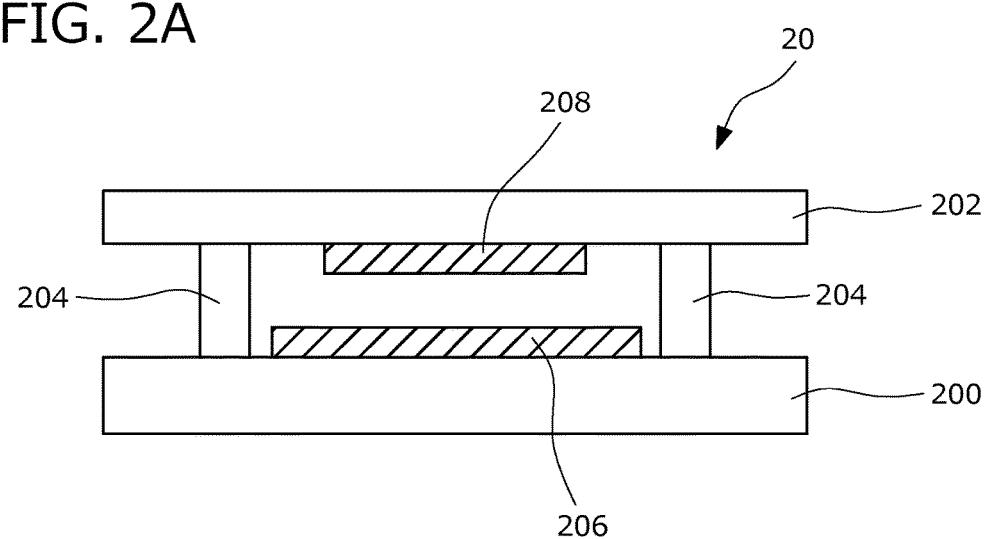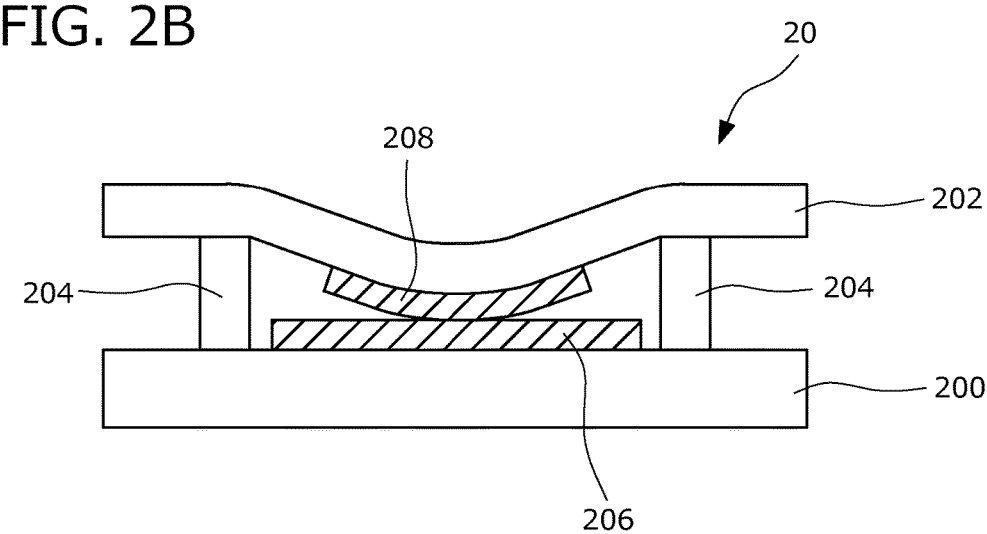

VEHICLE SEAT

CROSS REFERENCE TO RELATED APPLICATIONS

This application is the U.S. national phase of the International Patent Application No. PCT/JP2013/061521, filed Apr. 18, 2013, which claims the benefit of the Japanese Patent Application No. 2012-095789, filed Apr. 19, 2012, the entire content being incorporated herein by reference.

BACKGROUND

Disclosed herein is a vehicle seat that is capable of measuring respiration.

The physical condition of a driver is closely relevant to safe driving of a vehicle. To this end, for example, Japanese Patent Document No. 2011-156196 A ("the '196 Patent Document") discloses a technique for monitoring a driver's physical condition by providing a device for detecting physical information such as driver's respiration in a vehicle seat.

Specifically, the '196 Patent Document discloses a biological information detection device that includes a sensor provided in a seat cushion and detects a change in a load of a seated person, and an arithmetic operation unit that computes biological information on the basis of the change in the load obtained by the sensor. This sensor is constituted by a long piezoelectric film that detects a deformation in a length direction or a bending direction. This sensor is arranged in the seat cushion a front-to-back direction which is preset so that a length direction of the sensor matches the front-to-back direction of the seat cushion over a position facing the buttocks of a seated person. This biological information detection device detects respiration or heartbeats by causing the sensor to detect the change in the load applied from the seated person, and causing the arithmetic operation unit to compute the biological information on the basis of a detected signal.

To detect a pressure change in response to the respiration right under the buttocks of the seated person, it is necessary to use a sensor capable of detecting a bending deformation such as the sensor disclosed in the '196 Patent Document. Furthermore, the load resistance performance of the sensor and the detection accuracy of the sensor are normally contradictory properties such that an improvement in one tends to diminish the other. For this reason, a load sensor detecting only the load perpendicular to a detection surface is disadvantageous in measuring a respiration signal right under the buttocks of the seated person with high accuracy.

SUMMARY

The disclosure herein has been provided in view of these problems, and addresses providing a vehicle seat capable of expanding the applicable range of a sensor and detecting a respiration signal of a seated person with high accuracy.

The problem can be solved by the vehicle seats described below. The vehicle seat includes: a seat cushion; and a measuring device including at least one sensor that is provided in the seat cushion and that detects a pressure signal from a load applied from a seated person, and an arithmetic operation device that computes the detected pressure signal to obtain a respiration signal of the seated person, the measuring device measuring respiration of the seated person, wherein the sensor is provided to be along an edge of a contact portion between the seat cushion and buttocks of the seated person, and transmits the detected pressure signal to the arithmetic operation device.

Since the sensor is provided in the seat cushion to be along the edge of the contact portion between the seat cushion and the buttocks of the seated person as described above, it is possible to expand a sensor applicable range and ensure highly accurate measurement.

It is preferable that the sensor has a detection surface, a lengthwise length of the detection surface being different from a crosswise length, the detection surface being arranged so that a lengthwise direction of the sensor is along the edge.

By doing so, it is possible to enlarge the range of the detection surface of the sensor at a position along the edge of the contact portion between the seat cushion and the buttocks of the seated person, and ensure highly accurate and stable measurement.

It is preferable that the sensor is provided on a back side of the edge if a vehicle forward direction is a front direction.

By doing so, it is possible to decrease the probability that a heavy load is applied from the buttocks of the seated person to the sensor.

It is preferable that at least two sensors are provided on a front side and a back side, respectively, if a vehicle forward direction is a front direction.

By doing so, it is possible to ensure highly accurate and stable measurement irrespective of the physical difference among seated people.

It is preferable that at least a pair of sensors are arranged to spread to one side in a front-to-back direction if a vehicle forward direction is a front direction.

By doing so, it is possible to enlarge the range of the detection surface of the sensor at a position along the edge of the contact portion between the seat cushion and the buttocks of the seated person, and ensure highly accurate and stable measurement.

The sensor may have a curved shape.

By doing so, it is possible to enlarge the range of the detection surface of the sensor at a position along the edge of the contact portion between the seat cushion and the buttocks of the seated person, and ensure highly accurate measurement.

It is preferable that the sensor is provided so that at least a part of the sensor is located backward of a region where a maximum load is applied to the seat cushion from the buttocks in a state in which the seated person is seated.

By doing so, it is possible to detect the respiration more accurately by providing the sensor backward of the region where the maximum load is applied.

It is preferable that the sensor includes a first sensor provided on the back side and a second sensor provided on the front side, and that the first sensor is arranged outward of the second sensor in a seat width direction.

By doing so, it is possible to more stably acquire suitable pressure signals corresponding to respiration signals irrespective of the physical difference among the seated people.

Furthermore, it is preferable that a plurality of sensors are provided as the sensor, and that the measuring device measures the respiration of the seated person by selecting data that reflects the respiration from among data detected by the plurality of sensors.

By doing so, it is possible to stably measure the respiration.

Since the sensor is provided in the seat cushion to be along the edge of the contact portion between the seat cushion and the buttocks of the seated person as described above, it is possible to expand a sensor applicable range and ensure highly accurate measurement.

BRIEF DESCRIPTION OF DRAWINGS

FIG. 1 is a perspective/schematic block diagram that shows an overall configuration of a vehicle seat according to an embodiment.

FIG. 2A is a cross-sectional view showing a state of a sensor in a state in which a seated person is absent.

FIG. 2B is a cross-sectional view showing a state of the sensor in a state in which the seated person is present.

DETAILED DESCRIPTION

Figure 3:
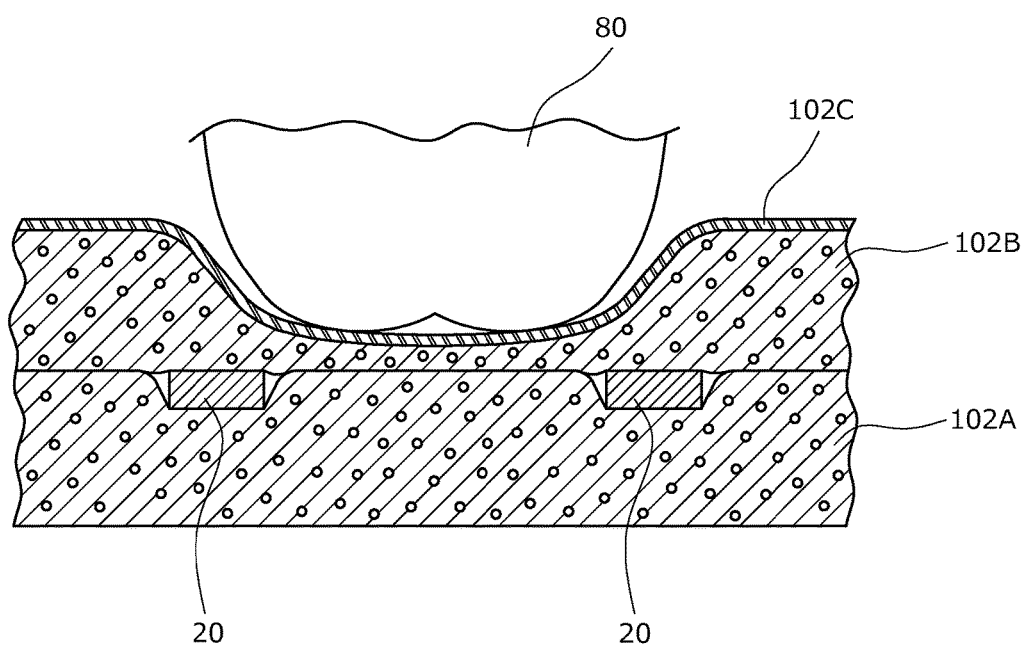
FIG. 3 is a cross-sectional view showing the arrangement of sensors in a cross-section of a seat cushion.

A vehicle seat according to various embodiments of the present invention will be described specifically hereinafter with reference to the accompanying drawings.

As shown in FIG. 1, a vehicle seat 10 according to the embodiment includes a seat cushion 102 that is a region on which a seated person 80 (FIG. 3, FIG. 4) is seated, a seat back 104 that is rotatably attached to a back portion of the seat cushion 102 and that is a region on which the seated person 80 leans, and a respiration measuring device 12 provided in the seat cushion 102 and including a sensor 20, to be described later.

As shown in FIG. 3, the seat cushion 102 includes a urethane pad 102A, a urethane slab 102B adhesively bonded to an upper surface of the urethane pad 102A, and a skin 102C provided to further cover the urethane slab 102B.

The respiration measuring device 12 includes the sensor 20 provided near an upper surface of the seat cushion 102, and an arithmetic operation device 70C that generates a waveform relating to respiration on the basis of a signal obtained from the sensor 20.

The sensor 20 is a resistance-sensitive sensor having a circular detection surface at a diameter of about 8 mm and a thickness of about 1 mm. As shown in FIG. 2A, the sensor 20 includes a lower film sheet 200 having an upper surface on which an electrode 206 is bonded, an upper film sheet 202 having a lower surface on which an electrode 208 is bonded and having flexibility, and spacers 204 provided to separate the lower film sheet 200 from the upper film sheet 202 at predetermined intervals. The electrodes 206 and 208 are constituted by, for example, a combination of silver, carbon, and pressure-sensitive ink.

In the sensor 20 configured as described above, the upper film sheet 202 is closer to the lower film sheet 200 by deforming downward in response to a magnitude of a pressure applied from the upper surface, and the electrode 208 contacts the electrode 206. After contact, if a contact resistance generated between the electrodes 206 and 208 increases, an electric resistance value between the electrodes decreases. The sensor 20 transmits an electrical signal relating to this electric resistance value to the arithmetic operation device 70C, to be described later. The arithmetic operation device 70C computes the pressure on the basis of the electric signal relating to the electric resistance value, and measures a respiration signal on the basis of the computed pressure.

As shown in FIG. 3, the sensor 20 is arranged between the urethane pad 102A and the urethane slab 102B.

Figure 4:
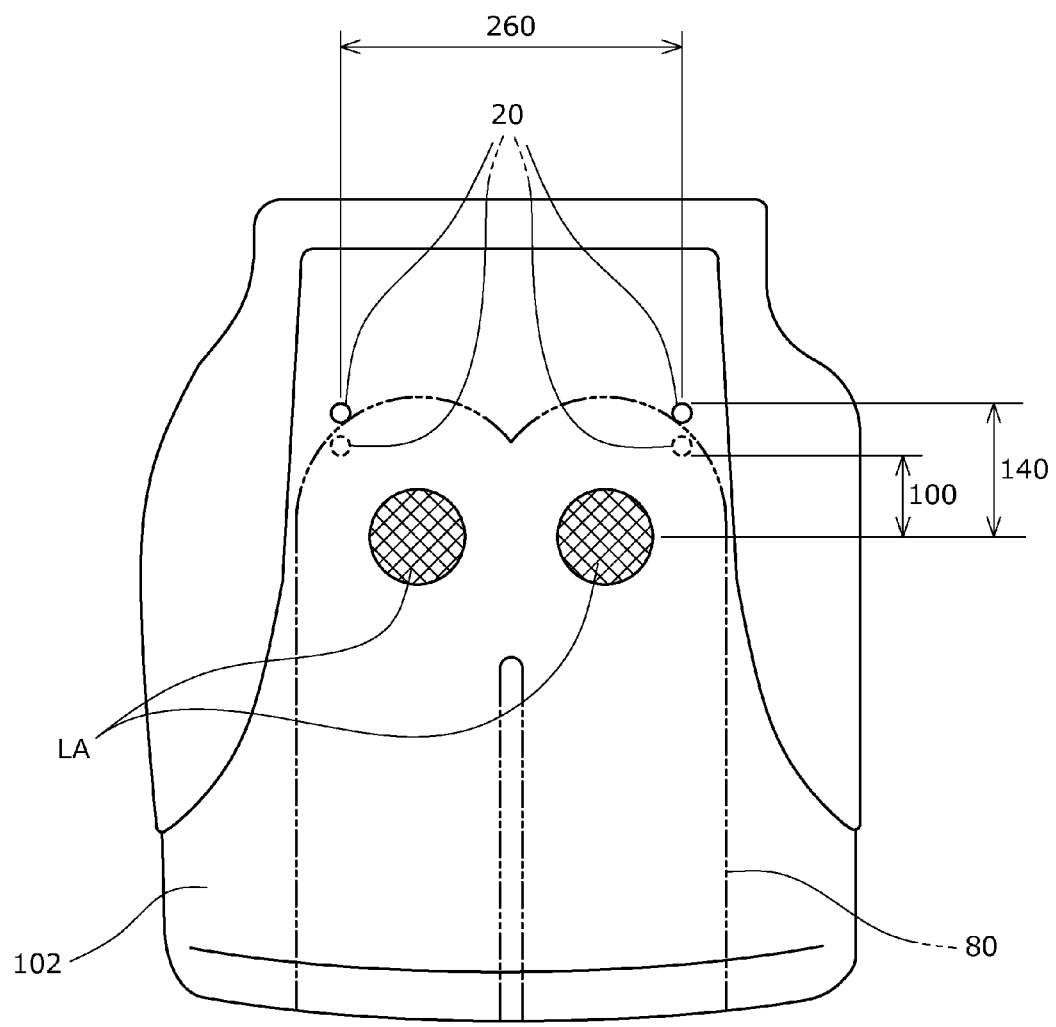
FIG. 4 is a pictorial schematic diagram showing the arrangement of the sensors in a plan view.

As shown in FIG. 4, two sensors 20 are provided to be along a back edge (hereinafter, a vehicle forward direction is referred to as "front direction" and an opposite direction to the vehicle forward direction is referred to as "back direction") of a surface (hereinafter, "seated-person contact surface") on which the buttocks of the seated person 80 contact the skin 102C of the seat cushion 102 in a plan view. Specifically, the two sensors 20 are arranged such that a center-to-center interval between the sensors 20 in a width direction of the seat cushion 102 is about 260 mm. Furthermore, each of the sensors 20 is provided within a range of about 100 to 140 mm backward of a center of a maximum load area LA to which a maximum load is applied from the buttock of the seated person 80. This maximum load area LA is an area specified on the basis of a dummy compliant with the SAE standard. In FIG. 4, to clearly show this arrangement range of the sensors 20, the sensors 20 arranged on a front end in the arrangement range are indicated by broken lines as virtual lines. Note that the sensors 20 are indicated by solid lines in each drawing to clearly distinguish from the other lines unless specified otherwise.

As shown in FIG. 1, the arithmetic operation device 70C includes an arithmetic control CPU (Central Processing Unit) 70CA, a RAM (Random Access Memory) 70CB, and a ROM (Read Only Memory) 70CC. The electrical signals relating to the resistance values are input from the sensors 20 to the arithmetic operation device 70C, and the arithmetic operation device 70C outputs the respiration signal. Signals other than the respiration signal are filtered off from pressure signals. Specifically, vibration of the vehicle, pressure fluctuations of the seated person 80 due to braking operation and acceleration operation, and the other noise are eliminated from the pressure signals. Only the respiration signal is amplified, thereby extracting the respiration signal. In the embodiment, controls for extracting the respiration signal based on the pressure signals from the sensors 20, computing a respiration rate from the respiration signal, and the like in the respiration measuring device 12 are relevant components, but not specifically described herein since the configurations are not principal configurations for solving the problem.

The RAM 70CB temporarily stores therein parameters including signals under an arithmetic operation control and input/output signals. The RAM 70CB functions as a storage unit 700 that stores therein digital signals converted from the pressure signals and the other signals.

The ROM 70CC stores therein programs executed by the CPU 70CA and predetermined parameters. A waveform generation unit 702 that generates pressure waveform data from the resistance-value-related electrical signals obtained from the sensors 20, and a selection unit 704 that selects pressure waveform data corresponding to the respiration are recorded in the ROM 70CC as the programs.

Figure 5:
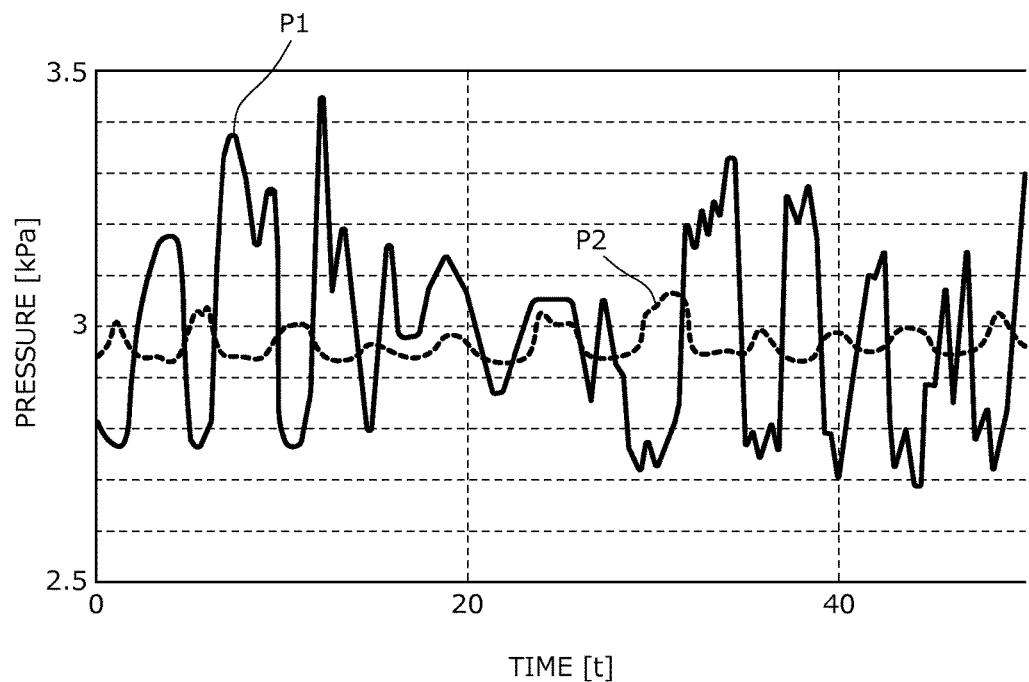
FIG. 5 is a graph that shows pressure waveforms based on electrical signals from two sensors.

The waveform generation unit 702 functions to generate pressure waveform data P1 and P2 (see FIG. 5) with a vertical axis representing pressure and a horizontal axis representing time on the basis of the resistance-value-related electrical signals obtained from the sensors 20 and stored in the storage unit 700.

The selection unit 704 functions to select the pressure waveform data synchronous with the respiration and indicating a fluctuating pressure equal to or higher than a predetermined value from between the pressure waveform data P1 and P2, and to set the selected pressure waveform data as respiration signal data. For example, as a selection basis, if the selection unit 704 is to select either the pressure waveform data P1 or P2, the selection unit 704 selects the pressure waveform data P1 on which a fluctuating pressure of about ±0.1 kPa appears periodically at intervals of about three to four seconds substantially identical to a cycle of the respiration. In a case of selecting the pressure waveform data synchronous with the respiration, the selection unit 704 is set to regard a respiration signal temporally long and having an extremely large pressure fluctuation such as a yawn as noise and to preclude the respiration signal from determination targets.

In the vehicle seat 10 according to the embodiment, the sensors 20 are arranged to be along the back edge of the seated-person contact surface in a plan view. Furthermore, the load from the seated person 80 is added to the sensors 20 via the skin 102C and the urethane slab 102B since the sensors 20 are arranged between the urethane pad 102A and the urethane slab 102B.

The sensors 20 can detect a very small pressure fluctuation accompanying the respiration since the sensors 20 are arranged not right under the buttocks but along the edge of the seated-person contact surface and a high pressure is not applied to the sensors 20. Furthermore, a high pressure resistance performance is not required of the sensors 20 since the sensors 20 are not arranged right under the buttocks. As a result, even if the sensors 20 are inexpensive sensors that cannot detect the bending deformation relative to the pressure detection surface but that can detect only the pressure in the perpendicular direction, it is possible to ensure high accuracy for the detection of the respiration signal. Moreover, a long service life can be ensured for the sensors 20 by reducing the pressure load applied to the sensors 20 by the arrangement of the sensors 20.

As shown in FIG. 1, the respiration measuring device 12 can be connected to the display D to display a respiratory state of the seated person. This enables the respiratory state and eventually a state of consciousness of the seated person 80 to be visually monitored. Furthermore, if an abnormality such as a decrease in an awakening degree or hyperpnoea is detected from the measured respiration signal, for example, an alarm is produced to make the seated person 80 or the other passenger auditorily sense the abnormality. Alternatively, by driving a vibrating motor, the seated person 80 or the other passenger can be made to tactually sense the abnormality, or by blinking a lighting device such as an LED, the seated person 80 or the other passenger can be made to visually sense the abnormality.

First Modification

In the above embodiment, it has been described that the sensors 20 each having the circular detection surface are provided along the edge of the seat contact surface of the seated person 80 in the vehicle seat 10. However, it suffices that the sensors are arranged along the edge of the seated-person contact surface, and the present invention is not limited to the sensors having the circular pressure detection surfaces. Sensors 22, 24, and 26 according to a first modification will next be described. In the following description, for making clearer the difference in features of the first modification from the embodiment, the same contents as those of the vehicle seat 10 according to the embodiment are not repeatedly described.

Figure 6:
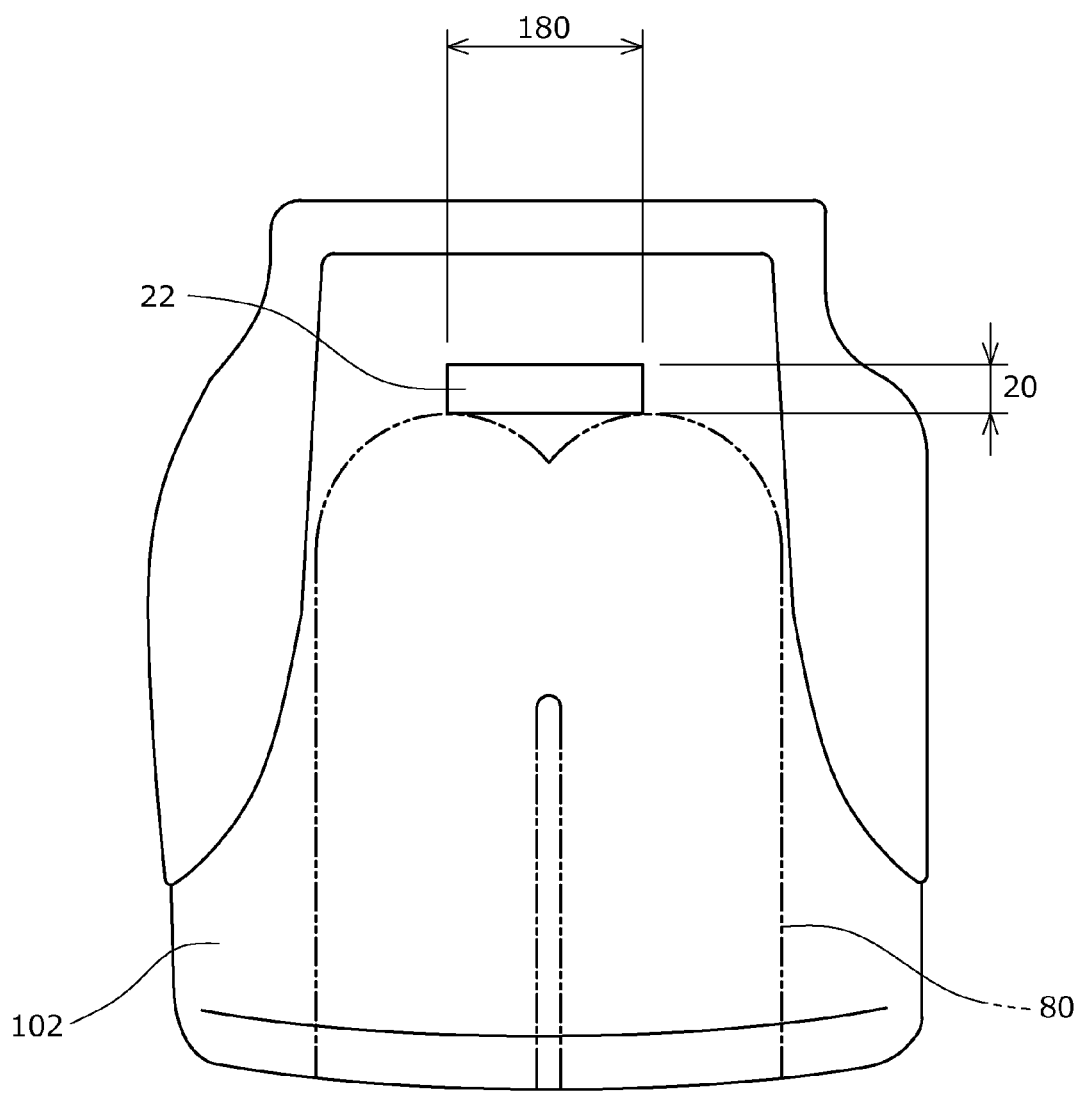
FIG. 6 is a plan view showing a shape and arrangement of sensors according to a first modification.

For example, as shown in FIG. 6, the sensor 22 has a rectangular pressure detection surface having short sides of about 20 mm and long sides of about 180 mm, and is arranged so that the long side is along the back edge of the seated-person contact surface.

Figure 7:
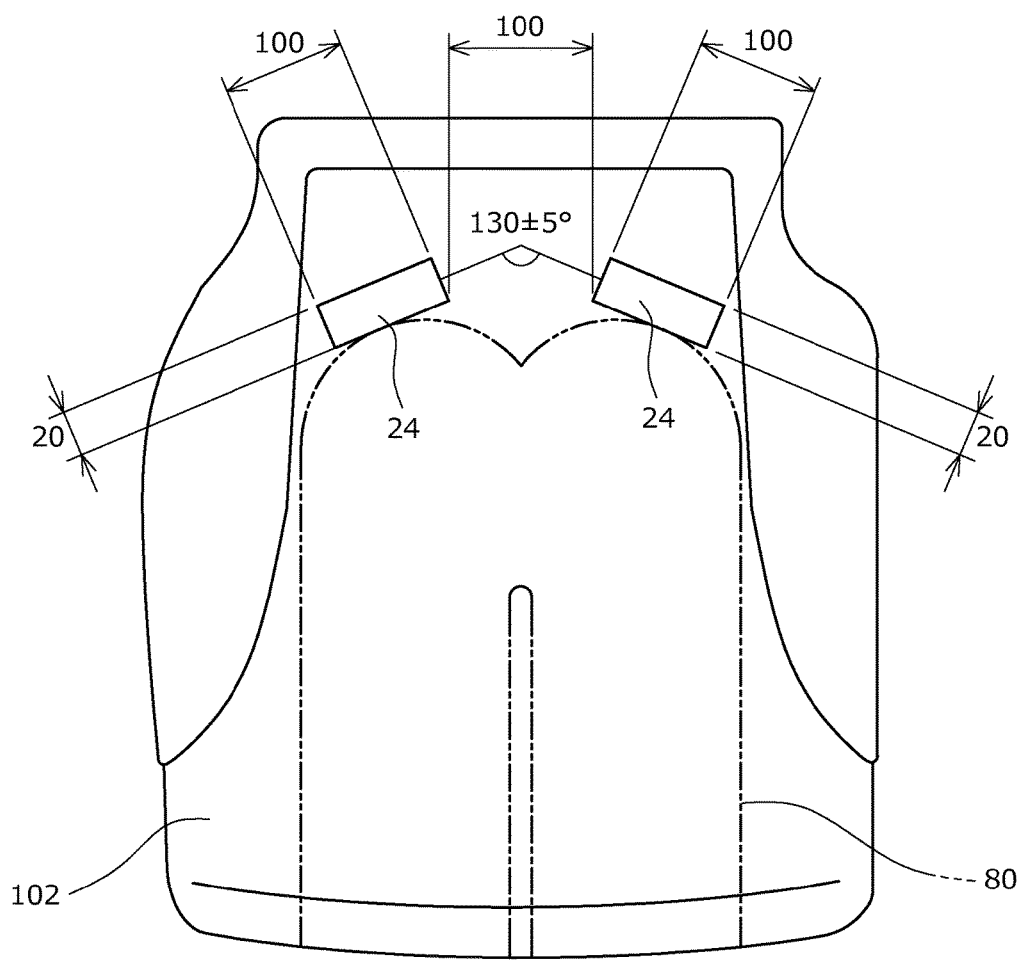
FIG. 7 is a plan view showing the shape and arrangement of the sensors according to another example.

As shown in FIG. 7, a pair of sensors 24 are arranged in a direction of spreading forward in a plan view. Specifically, each sensor 24 has a rectangular pressure detection surface having short sides of about 20 mm and long sides of about 100 mm, and is arranged so that the long side is along the back edge of the seated-person contact surface. Specifically, the paired sensors 24 form an angle of 130±5° forward therebetween symmetrically about a central axis extending in the front-to-back direction of the seat cushion 102, and are arranged at a distance of about 100 mm therebetween.

Since the sensors 24 are arranged as a pair in the direction of spreading forward in a plan view, it is difficult to let the buttocks away from the detection surfaces by as much as the angle as compared with the sensor 22 with the long side arranged in the width direction of the seat cushion 102 if the buttocks move in the front-to-back direction in response to a change in a posture of the seated person 80. That is, it is possible to more stably acquire the highly accurate respiration signal.

Figure 8:
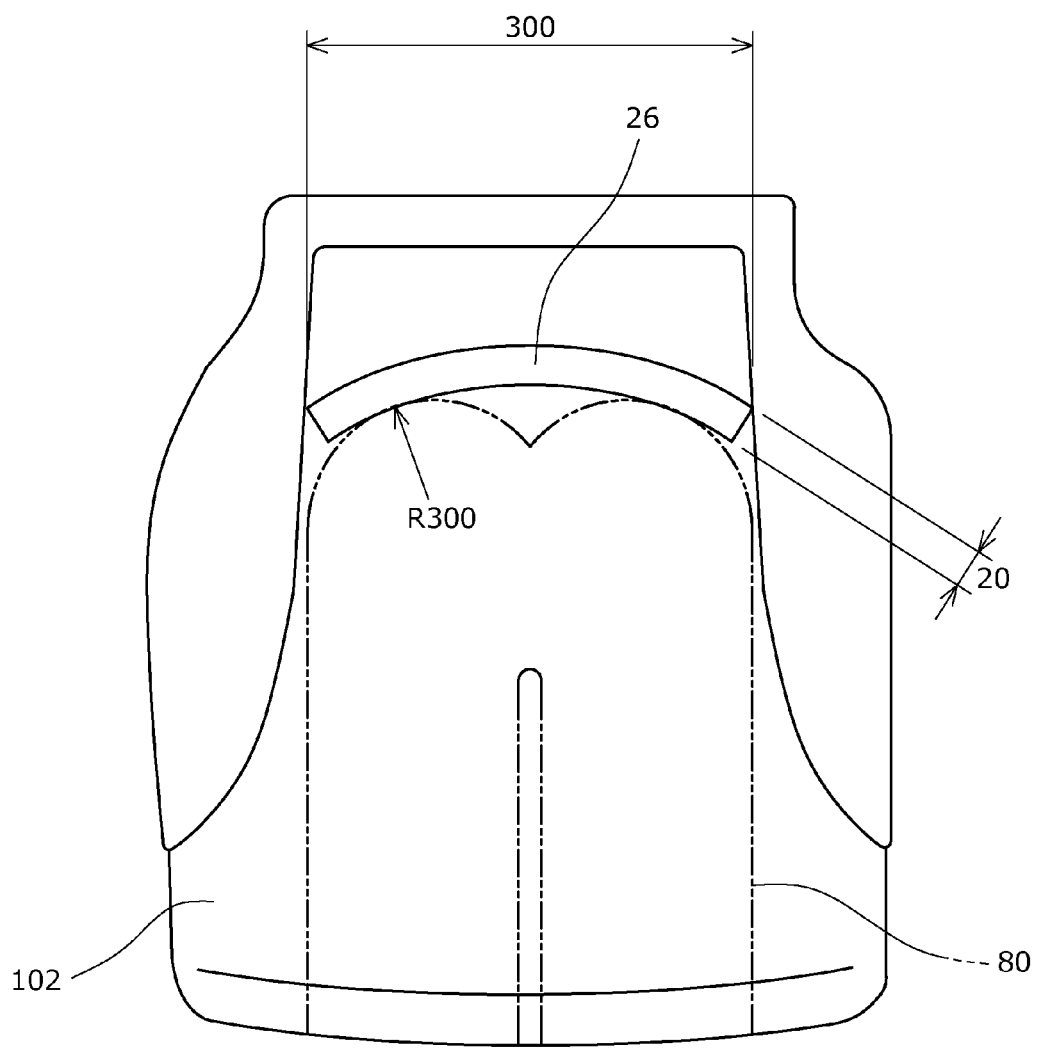
FIG. 8 is a plan view showing the shape and arrangement of the sensors according to another example.

As shown in FIG. 8, the sensor 26 has a curved circular-arc pressure detection surface at a width of about 20 mm and a radius of curvature of about 300 mm, and is arranged so that a long side direction is along the back edge of the seated-person contact surface in a plan view.

Note that each of the sensors 22, 24, and 26 is arranged to fall within the range of about 100 to 140 mm backward of the center of the maximum load area LA similarly to the sensor 20.

Furthermore, each of the sensors 22, 24, and 26 is arranged so that the long side direction is along the edge of the seated-person contact surface in a plan view. This can make the detection surface along the edge of the seated-person contact surface wider and, therefore, suppress each of the sensors 22, 24, and 26 from being in a no-load state even if the posture of the seated person changes. That is, an increase in the probability that an appropriate pressure signal synchronous with the respiration can be detected enables the stable acquisition of the pressure signals.

As described later, each of the sensors 22 and 26 may be an assembly of a plurality of sensors. If the arithmetic operation device 70C includes one sensor, the arithmetic operation device 70C does not need the selection unit 704 since there is no need to provide the function of selecting one of the detected pressure signals.

Moreover, the contact with the seated person 80 is often non-uniform in the width direction of the seat cushion 102 such as, for example, a state in which the seated person 80 is cross-legged. In this case, the acquired pressure signal is sometimes low if the arithmetic operation device 70C includes one sensor. In such a case, the two or more sensors 20 or 24 provided at the same position in the front-to-back direction could avoid the influence of the non-uniform contact in the width direction on the acquisition of the pressure signals. As specific processing, the arithmetic operation device 70C can acquire a stable respiration signal by selecting the waveform of the pressure signal synchronous with the respiration from between those detected waveform of the pressure signal by the two sensors.

Second Modification

Sensors 22R and 22F, 32R and 32F, 42R and 42F, 26R and 26F, 24R and 24F, and 28R and 28F according to a second modification to be described below are characterized by being arranged in the seat cushion 102 in the front-to-back direction thereof in view of a seated person 80L of a large build and a seated person 80S of a small build who are physically different. The seated person 80S of the small build is, for example, one of about 150-cm-tall Japanese female adults who comprise about the bottom 5% of the population. The seated person 80L of the large build is, for example, one of about 190-cm-tall American male adults who comprise about the top 5% of the population.

Figure 9:
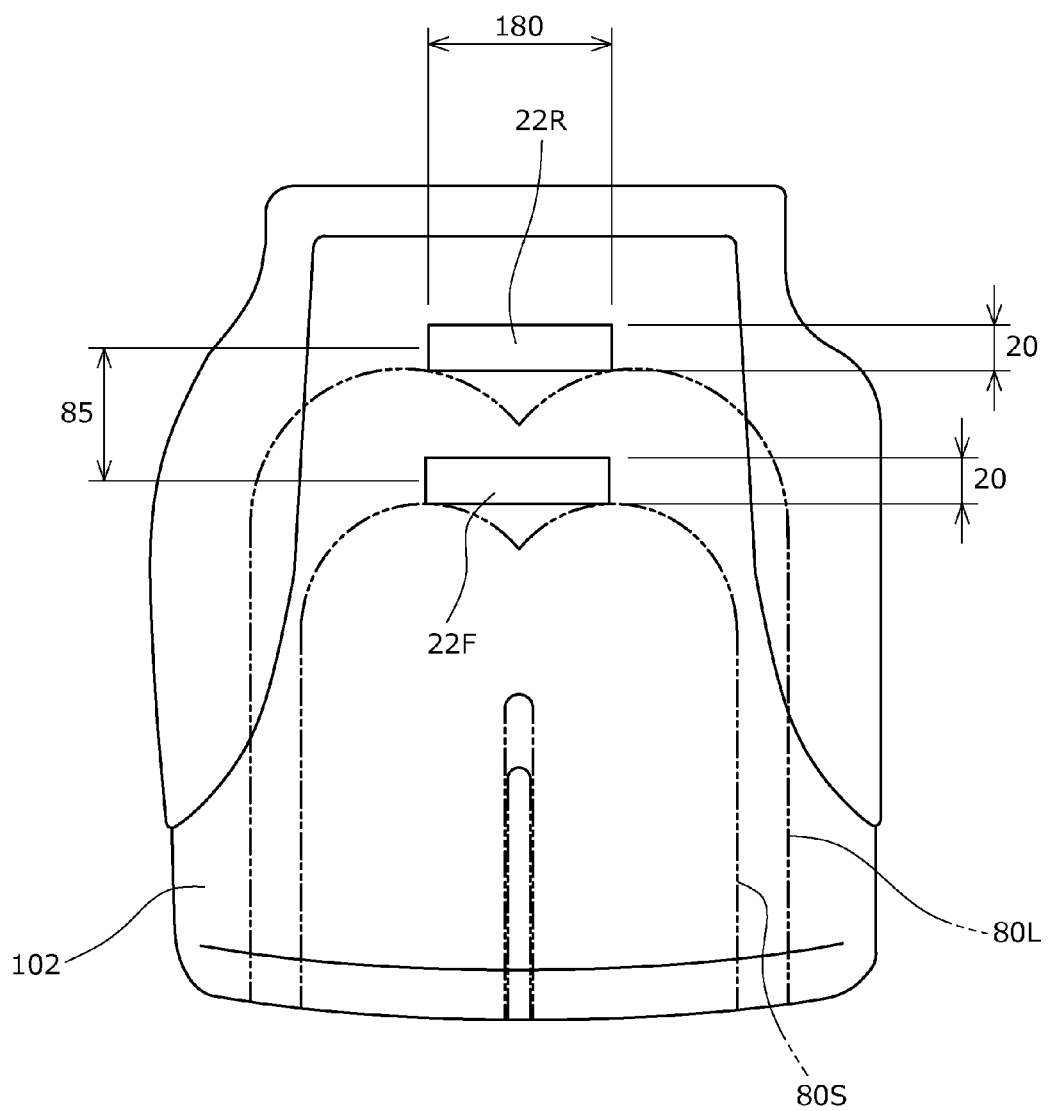
FIG. 9 is a plan view showing a shape and arrangement of sensors according to a second modification.

As shown in FIG. 9, the sensor 22R is equal in shape to the sensor 22 and arranged at the same position as that of the sensor 22. By contrast, the sensor 22F is equal in shape to the sensors 22 and 22R, arranged at the same position as those of the sensors 22 and 22R in the width direction of the seat cushion 102, and arranged forward of the sensor 22R at a distance of about 85 mm from the sensor 22R in the front-to-back direction.

The sensor 22F arranged as described above is along the edge of the seated-person contact surface of the seated person 80S in a plan view. Therefore, by thus arranging the sensors 22R and 22F, it is possible to appropriately acquire the respiration signal even for the seated person 80S of the small build in addition to that for the seated person 80L of the large build.

Because of the arrangement of the sensors 22R and 22F in two rows in the front-to-back direction as described above, it is possible to stably acquire the respiration signal even if the seated person 80L of the large build is seated forward on the seat cushion 102 or the seated person 80S of the small build is seated back thereon, for example. By adopting such a configuration, it is possible to detect the respirations of both the seated person 80L of the large build and the seated person 80S of the small build as long as the issue of cost to follow an increase in the number of parts is of less concern.

Figure 10:
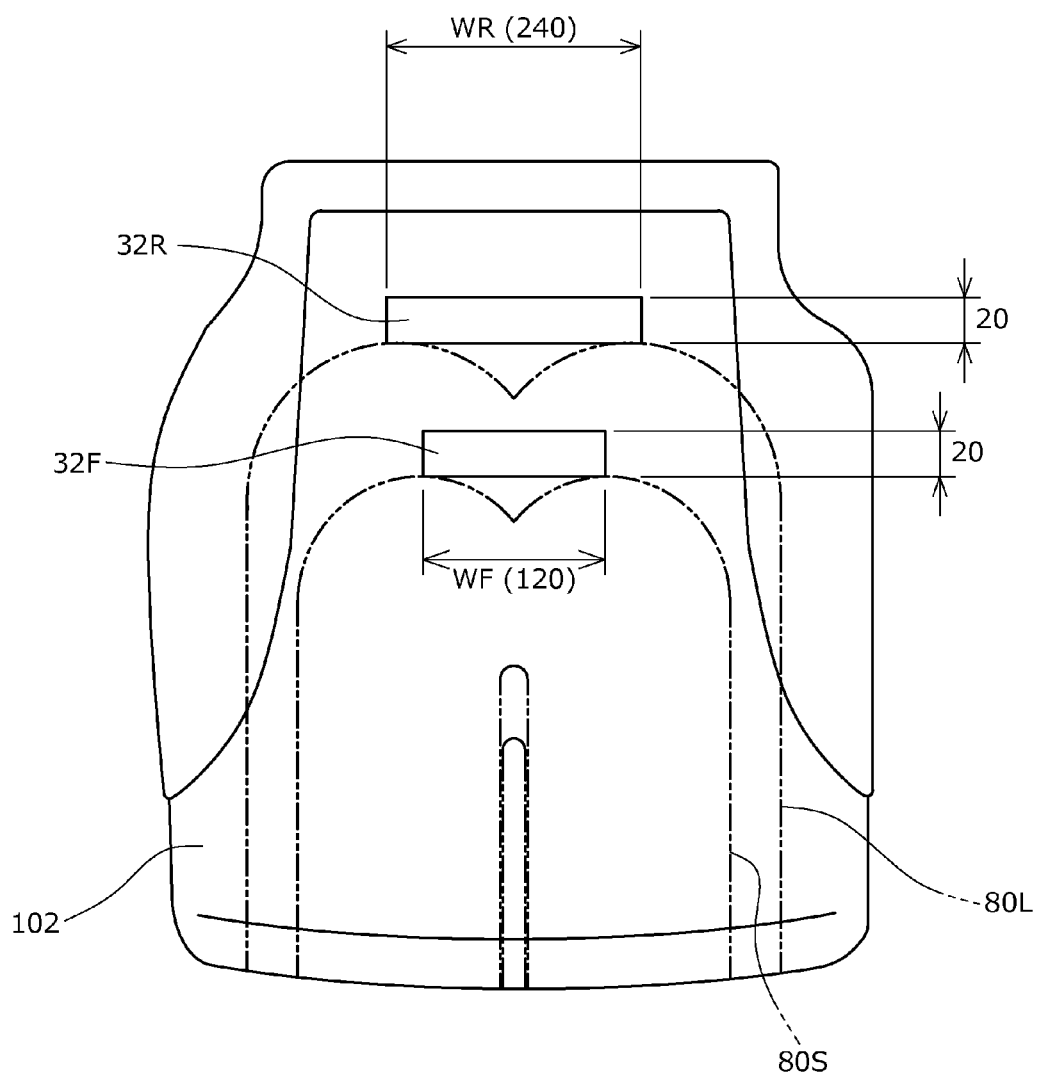
FIG. 10 is a plan view showing the shape and arrangement of the sensors according to another example.

Moreover, as shown in FIG. 10, a width WR of the back sensor 32R is preferably larger than a width WF of the front sensor 32F while the sensors 32R and 32F are arranged similarly to the sensors 22R and 22F. The width WR is about 240 mm and the width WF is about 120 mm. By so allocating the widths to the sensors 32R and 32F, the sensors 32R and 32F are configured to be along the respective edges of the seated-person contact surfaces of both the seated person 80S of the small build and the seated person 80L of the large build in similar ranges. That is, if it is assumed that both the seated person 80L of the large build and the seated person 80S of the small build are seated, it is more preferable to adopt this configuration.

Figure 11:
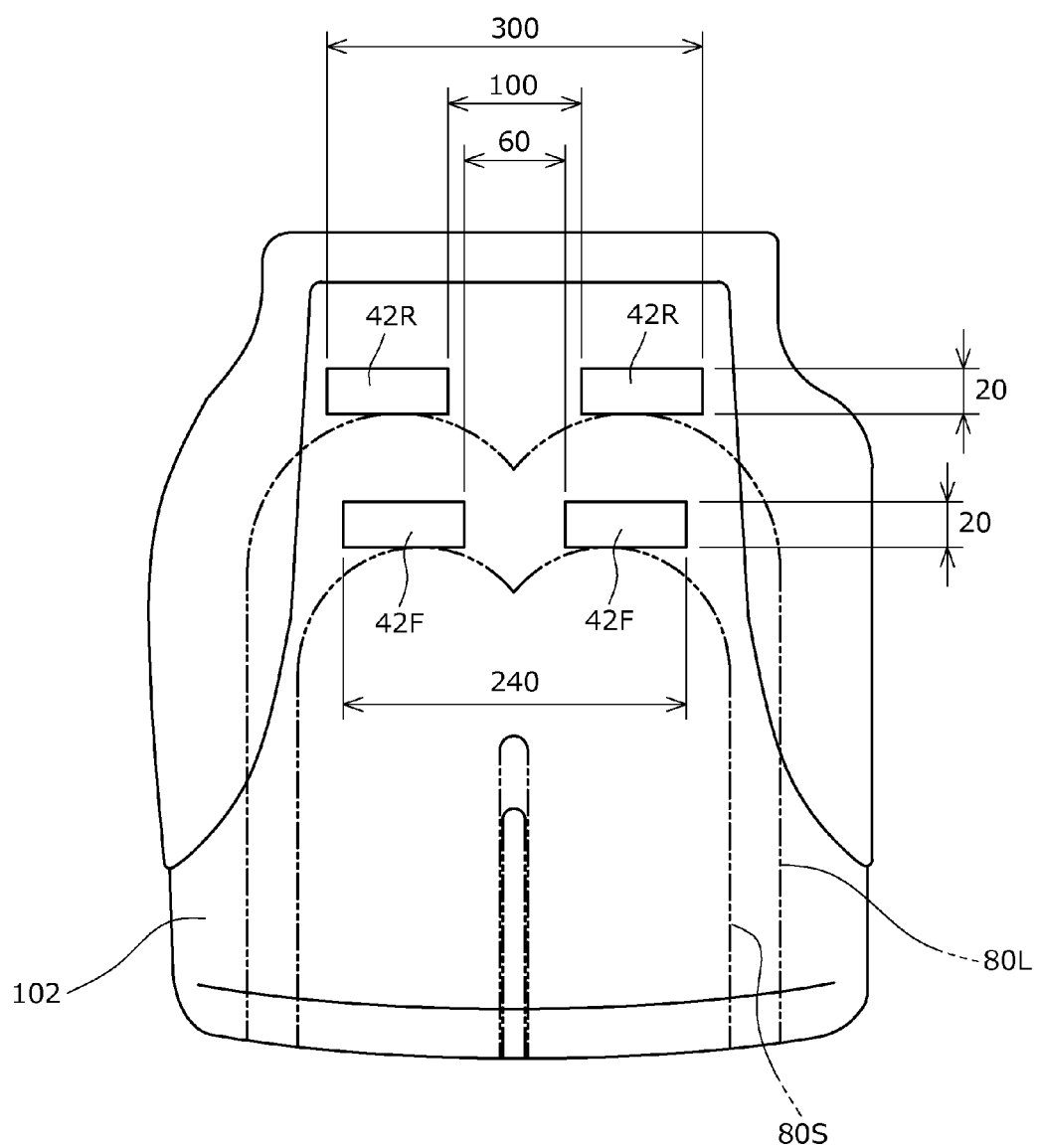
FIG. 11 is a plan view showing the shape and arrangement of the sensors according to another example.

As shown in FIG. 10, central portions of the sensors 32R and 32F in the width direction, that is, a central portion of the seat cushion 102 in the width direction is at a position separated from the edge of the seated-person contact surface. Owing to this, the central portions of the sensors 32R and 32F in the width direction are functionally less important. For example, therefore, instead of arranging the sensors in the central portion of the seat cushion 102 in the width direction, the sensors 32R and 32F may be arranged in a divided manner and two sensors may be arranged in the width direction such as the sensors 42R and 42F shown in FIG. 11.

Specifically, the two sensors 42R are arranged to be along the back edge of the seated-person contact surface of the seated person 80L at a central distance of about 100 mm in the width direction in a plan view. Furthermore, the two sensors 42R are arranged to have an outside distance of about 300 mm in the width direction. The two sensors 42F are arranged forward of the sensors 42R at a distance of about 85 mm in the front-to-back direction, and arranged to be along the back edge of the seated-person contact surface of the seated person 80S at a central distance of about 60 mm in the width direction. Furthermore, the two sensors 42F are arranged to have an outside distance of about 240 mm. The sensors 42R are arranged outward of the sensors 42F in the width direction. Owing to this, it is possible to stably acquire suitable pressure signal corresponding to the respiration signal irrespective of the physical difference between the seated person 80.

Figure 12:
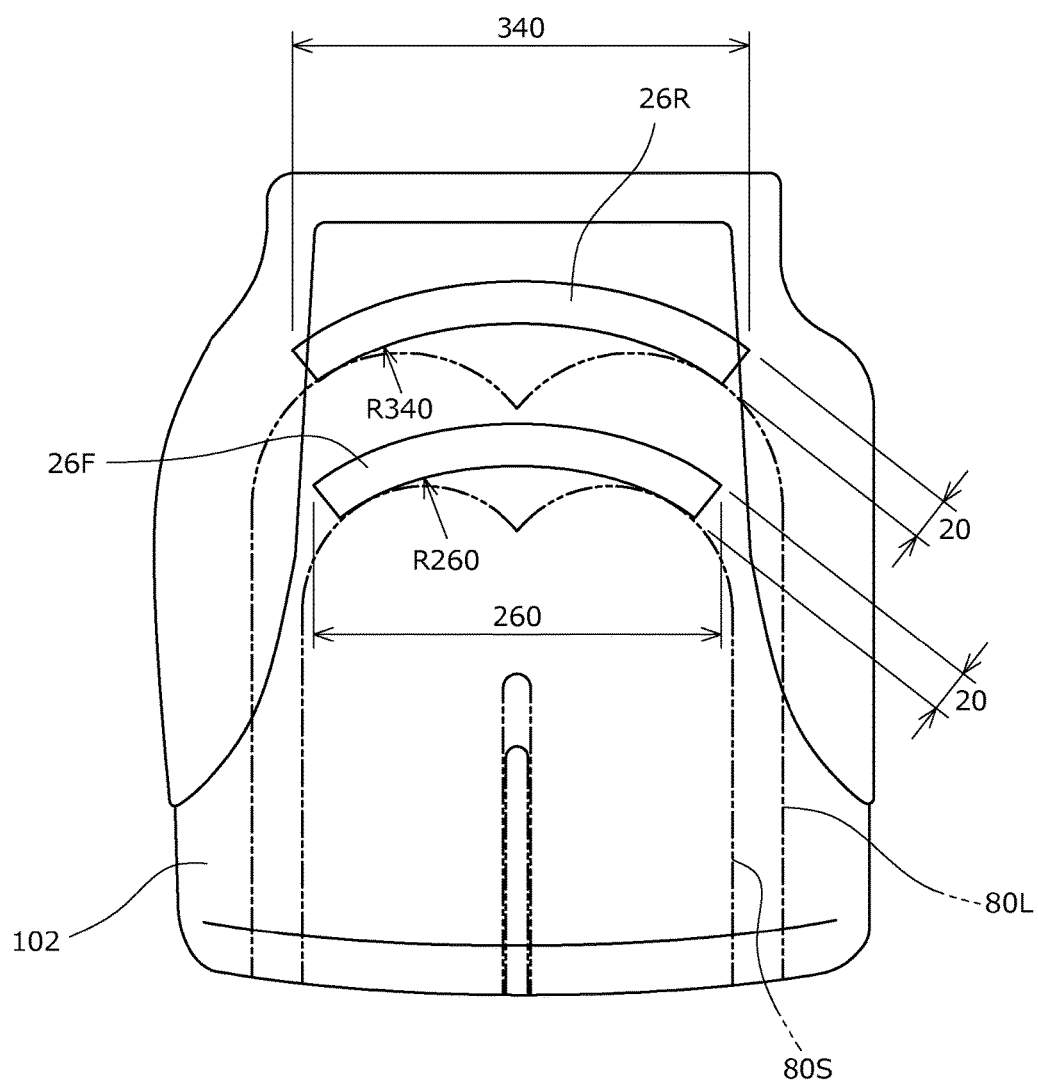
FIG. 12 is a plan view showing the shape and arrangement of the sensors according to another example.

As shown in FIG. 12, the sensors 26R and 26F each having a circular arc pressure detection surface may be arranged in similar ranges at similar distances to those described in the previous examples in the front-to-back direction. Specifically, the sensor 26R has the circular arc pressure detection surface at a width of about 20 mm and a radius of curvature of about 340 mm. The sensor 26F has the circular arc pressure detection surface at a width of about 20mm and a radius of curvature of about 260 mm. A dimension of the sensor 26R in the width direction is about 340 mm and that of the sensor 26F in the width direction is about 260 mm. That is, the sensor 26R is arranged outward of the sensor 26F in the width direction. Owing to this, it is possible to stably acquire suited suitable pressure signals corresponding to the respiration signal irrespective of the physical difference between the seated person 80.

Figure 13:
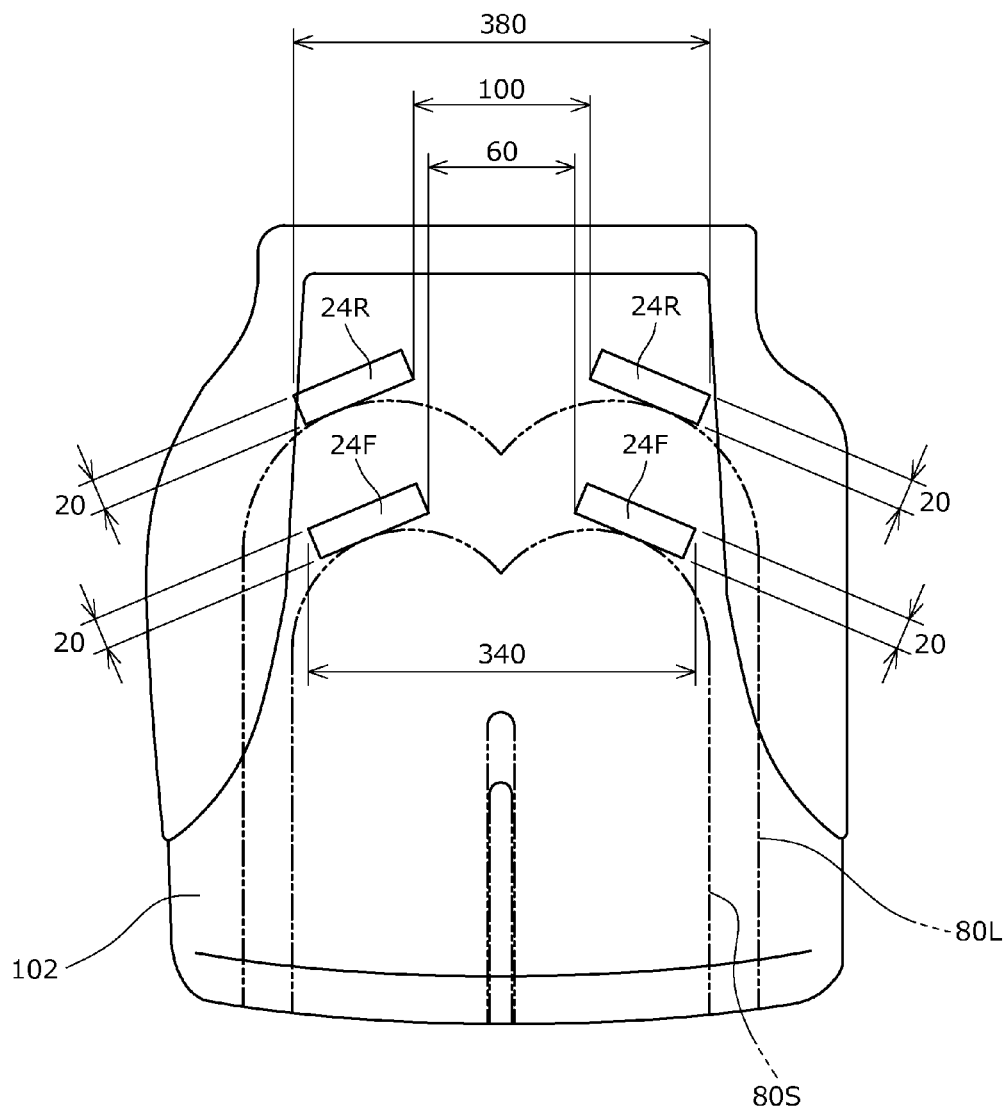
FIG. 13 is a plan view showing the shape and arrangement of the sensors according to another example.

Likewise, as shown in FIG. 13, a pair of sensors 24R arranged in the direction of spreading forward in a plan view and a pair of sensors 24F arranged forward of the sensor 24R in the direction spreading forward in a plan view may be arranged in similar ranges at similar distances to those described in the previous examples. Specifically, the pressure detection surface of each of the sensors 24R and 24F is a rectangular detection surface having short sides of about 20 mm and long sides of about 100 mm. The two sensors 24R are arranged to have an outside distance of about 380 mm in the width direction and to have a central distance of about 100 mm in the width direction. The two sensors 24F are arranged to have an outside distance of about 340 mm in the width direction, to form an angle of 130±0.5° forward therebetween symmetrically about the central axis extending in the front-to-back direction of the seat cushion 102, and to have a central distance of about 60 mm in the width direction. The sensors 24R are arranged outward of the sensors 24F in the width direction. Owing to this, it is possible to stably acquire suitable pressure signals corresponding to the respiration signal irrespective of the physical difference between the seated person 80. Moreover, the sensors 24F in the front row are more preferably provided at an angle equal to or smaller than 130±0.5° that is an angle of the sensors 24R in the back row to be along the buttocks of the seated person 80S of the small build.

Figure 14A:
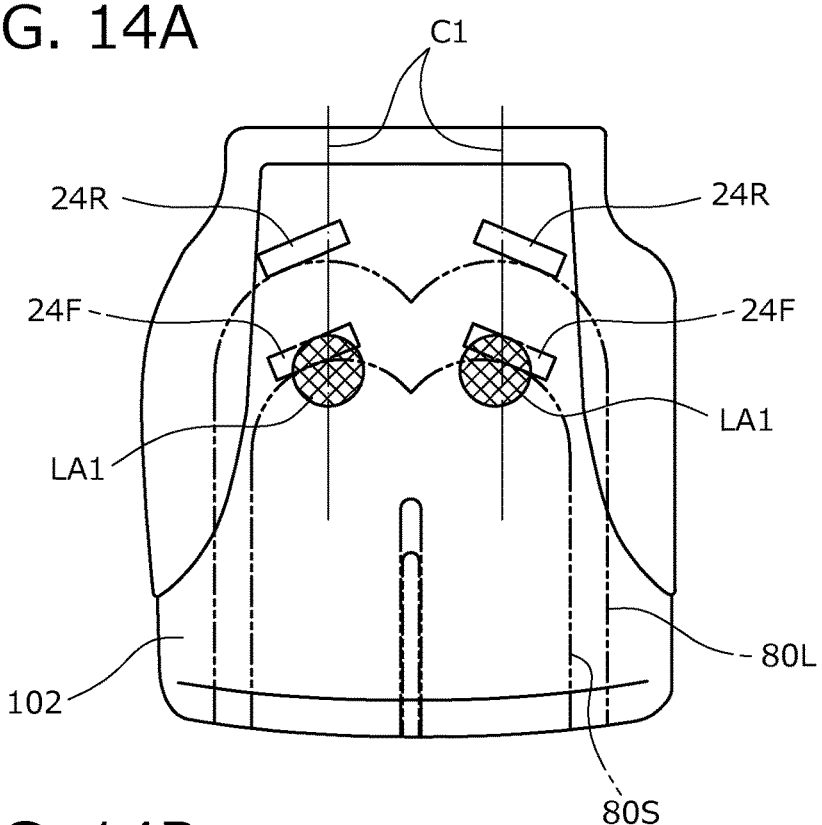
FIG. 14A is a plan view showing an arrangement relation between the sensors and maximum load areas according to another example.
Figure 14B:
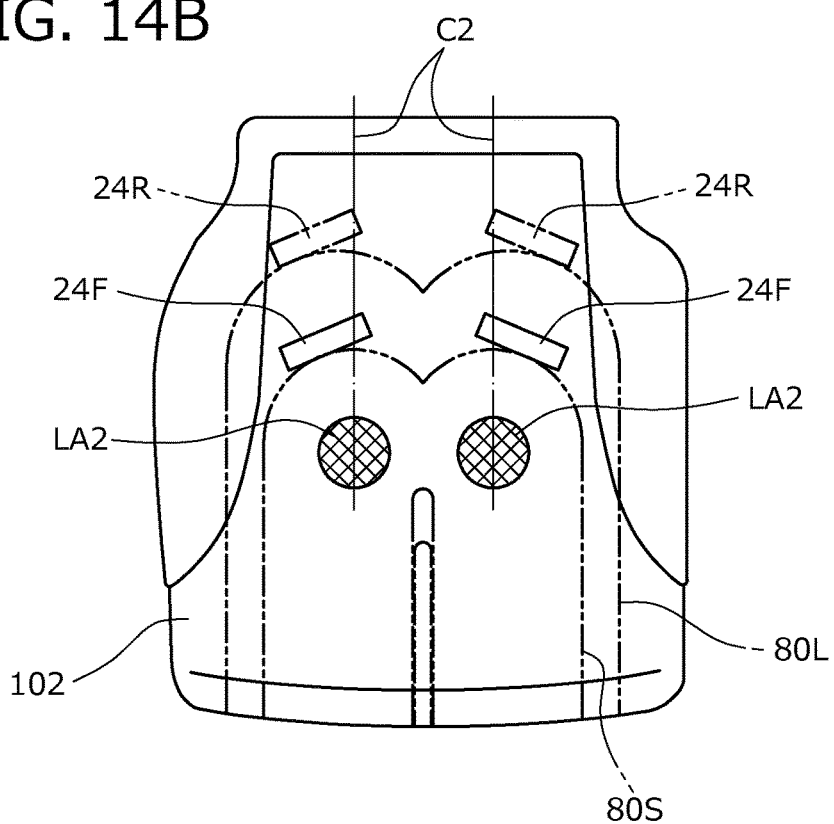
FIG. 14B is a plan view showing an arrangement relation between the sensors and maximum load areas according to another example.

As shown in FIG. 14A, it is desirable that the sensors 24R are arranged to cross centerlines C1 extending in the front-to-back direction in maximum load areas LA1 of the seated person 80L in a plan view. Likewise, as shown in FIG. 14B, it is desirable that the sensors 24F are arranged to cross centerlines C1 extending in the front-to-back direction in maximum load areas LA2 of the seated person 80S. By so arranging, it is possible to suitably detect the pressure signals corresponding to the respiration signals of the seated persons 80S and 80L.

Figure 15:
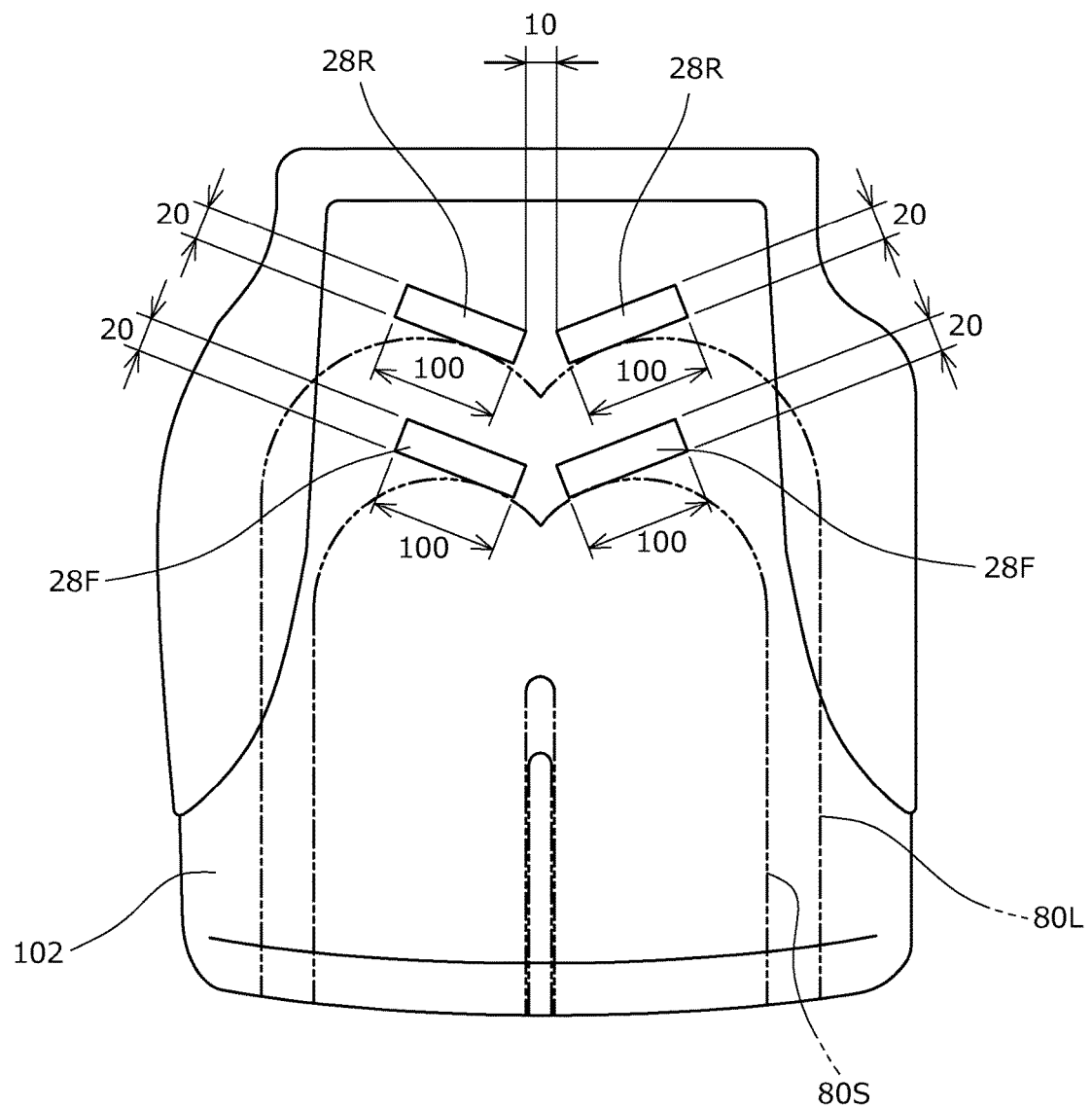
FIG. 15 is a plan view showing the shape and arrangement of the sensors according to another example.
Figure 16:
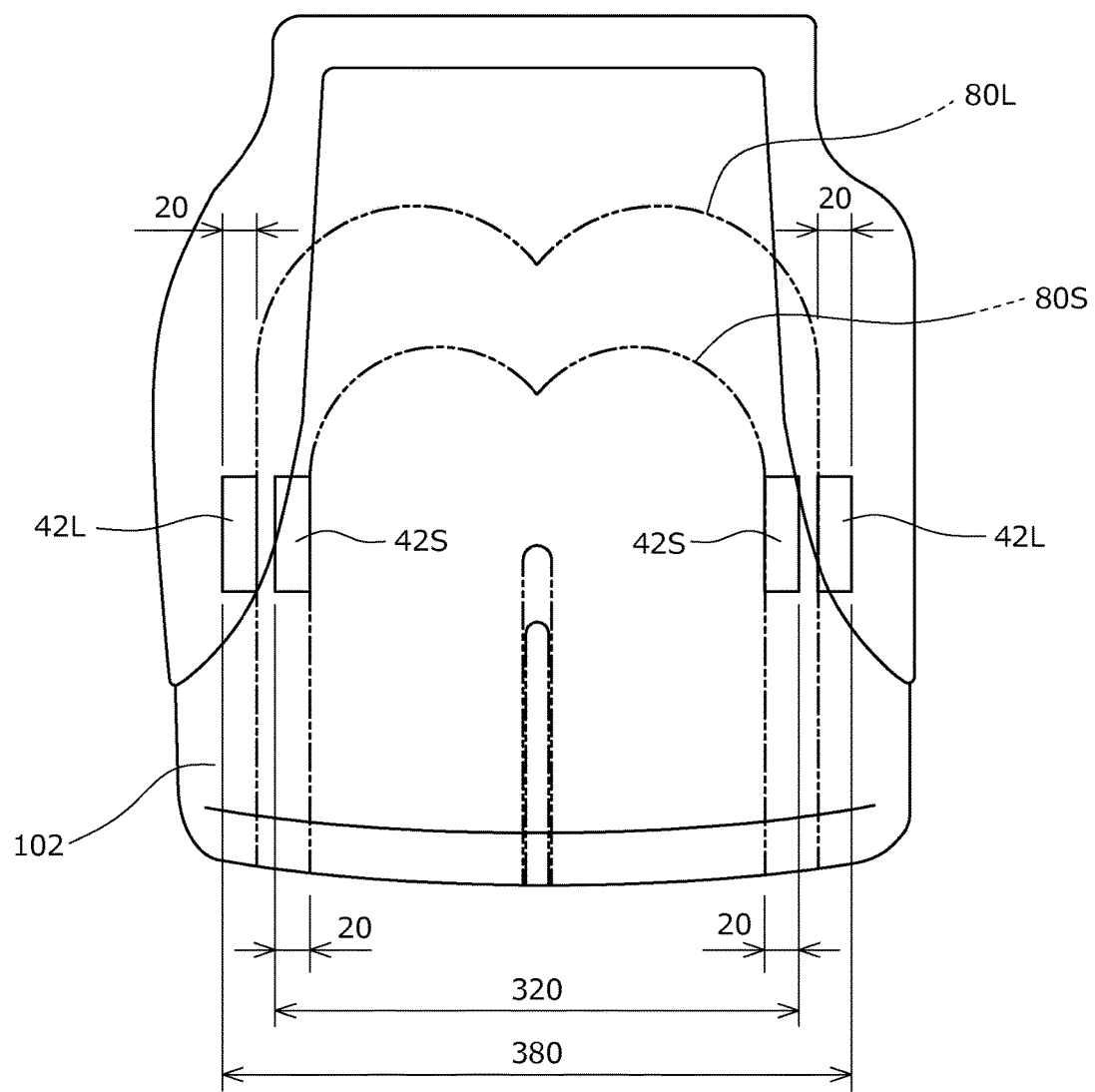
FIG. 16 is a plan view showing a shape and arrangement of sensors according to a third modification.

As shown in FIG. 15, the sensors may be constituted by a pair of back sensors 28R arranged in the direction of spreading backward in a plan view and a pair of front sensors 28F arranged forward of the sensors 28R at a distance of about 85 mm and arranged similarly in the direction of spreading backward in a plan view. The paired sensors 28R and the paired sensors 28F are arranged to form angles of about 130±5° backward, respectively. These sensors 28R and 28F are constituted by a pair of sensors each having a rectangular pressure detection surface having short sides of about 20 mm and long sides of about 100 mm. Each pair of the sensors 28R and 28F are arranged at a distance of about 10 mm in the width direction so that the long side direction is along the back edge of the seated-person contact surface, and arranged in similar ranges at similar distances to those in the previous examples.

Third Modification

In the embodiment and the modifications thereof, the sensors have been described as being provided to be along the back edge of the seated-person contact surface of the seated person 80. It suffices that the sensors are provided to be along the edge of the seated-person contact surface, and the present invention is not limited to such a configuration. For example, two sensors 42S according to a third modification are provided to be along side edges of the seated-person contact surface of the seated person 80S, respectively, and two sensors 42L are provided to be along side edges of the seated-person contact surface of the seated person 80L, respectively. That is, the sensors 42S are provided for detecting the respiration signal of the seated person 80S of the small build whereas the sensors 42L are provided for detecting the respiration signal of the seated person 80L of the large build.

Specifically, each of the sensors 42S and 42L has a rectangular detection surface having short sides of about 20 mm and long sides of about 100 mm. The sensors 42S and 42L are arranged in the seat cushion 102 so that the long side direction matches the front-to-back direction. The two sensors 42S are arranged to have an outside distance of about 320 mm in the width direction. The two sensors 42L are arranged to have an outside distance of about 380 mm in the width direction. By so arranging, it is possible to enlarge a pressure detection range in the front-to-back direction. Owing to this, it is possible to stably detect the respiration signal even if the posture of the seated person 80 changes such as a case where the seated person 80 is seated forward on the seat cushion 102 or a case where the seated person 80 is seated back thereon. That is, it is possible to suitably detect the respiration signal even if the posture frequently changes due to a continuous seated state for a long time.

By adopting such a configuration, it is possible to detect the respirations of both the seated person 80L of the large build and the seated person 80S of the small build as long as the issue of cost to follow an increase in the number of parts is of less concern. Moreover, it is possible to stably detect the respirations without influence of the change of the posture between the case where the seated person is seated back on the seat cushion 102 and the case where the seated person is seated forward thereon.

Figure 17A:
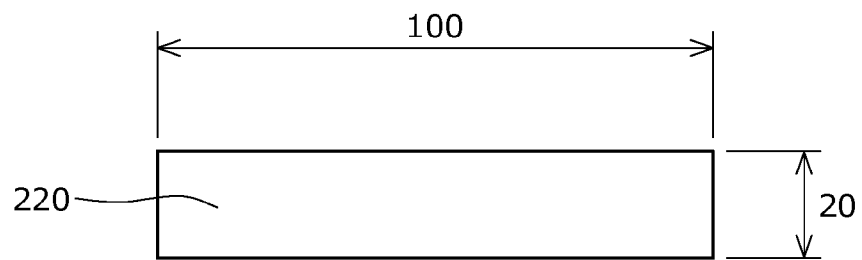
FIG. 17A is a pictorial view that shows a rectangular detection surface of the sensor.
Figure 17B:
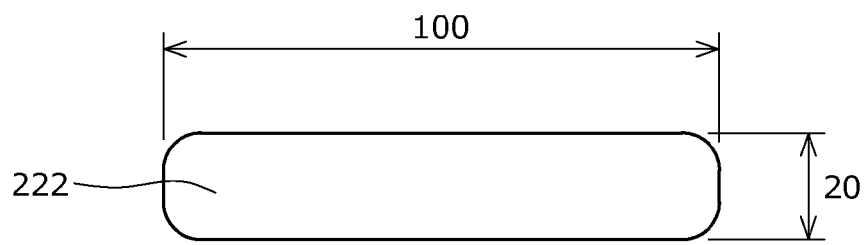
FIG. 17B is a pictorial view that shows a chamfered rectangular detection surface of the sensor.
Figure 17C:
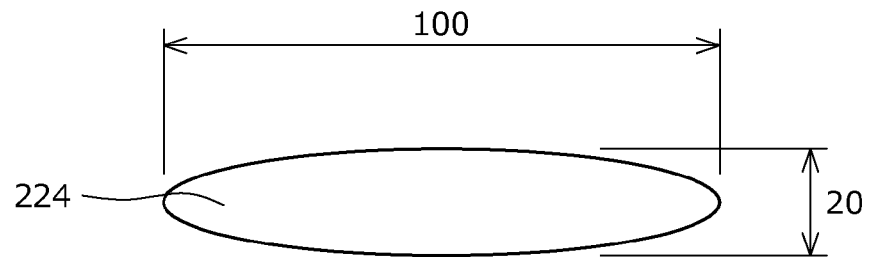
FIG. 17C is a pictorial view that shows an elliptical detection surface of the sensor.

While it has been described above that the detection surface of the sensor is the rectangular or circular arc surface, it suffices that the detection surface has long sides and short sides. For example, the detection surface is not limited to a rectangular detection surface 220 as shown the detection surface of the sensors 24 in FIG. 17A but may be a chamfered rectangular detection surface 222 as shown in FIG. 17B or may be an elliptical detection surface 224 as shown in FIG. 17C.

Figure 18:
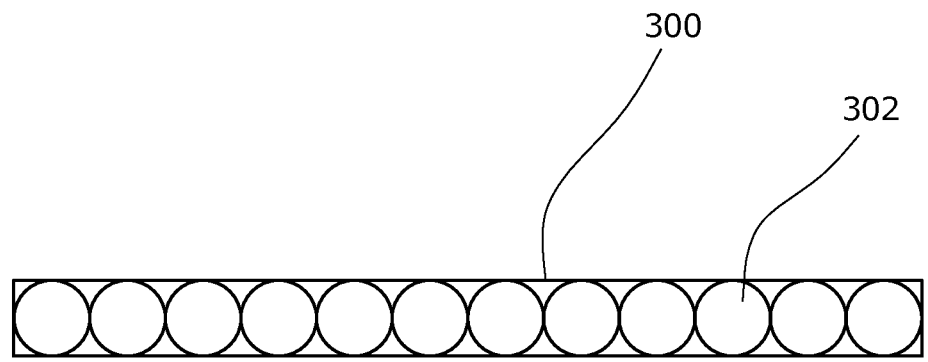
FIG. 18 is a pictorial view that shows a sensor group.

Moreover, the sensor that has been described above as having the rectangular detection surface may be a sensor group 300 constituted by a plurality of sensors 302 each having a circular detection surface as shown in FIG. 18. With this configuration, it is possible to select the pressure signal corresponding to the respiration signal from among those of the plurality of sensors 302 and acquire the respiration signal more stably.

Figure 19:
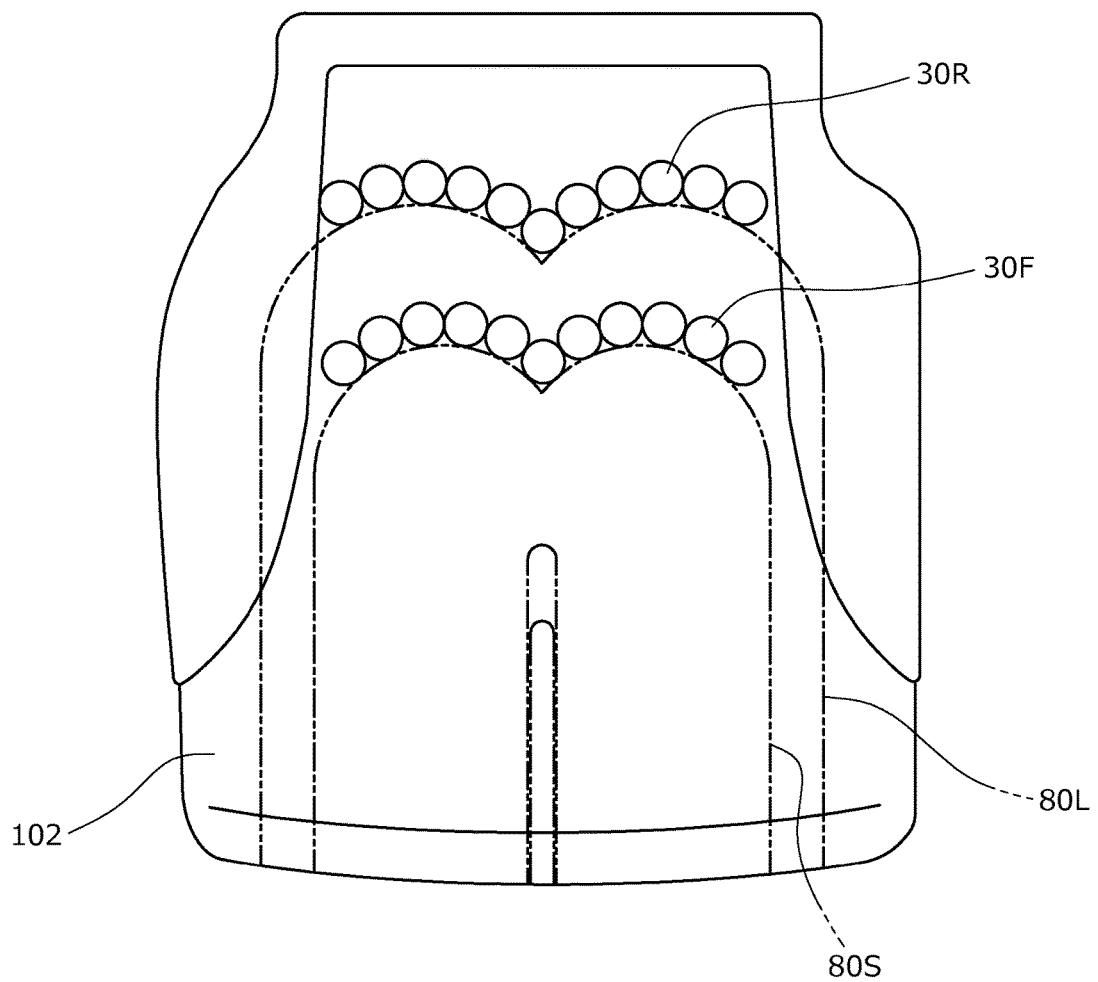
FIG. 19 is a plan view showing a shape and arrangement of sensors according to another example.

As shown in FIG. 19, a plurality of sensors 30R each having a circular detection surface may be arranged in a curved fashion along the back edge of the seated-person contact surface of the seated person 80L. Likewise, a plurality of sensors 30F each having a circular detection surface may be arranged in a curved fashion along the back edge of the seated-person contact surface of the seated person 80S.

Furthermore, it suffices that the sensor is arranged along the edge of the seated-person contact surface, and a type of the sensor is not limited to the resistance-sensitive sensor described above but a strain gauge sensor and the like are also available.

The present invention is not limited to the embodiment and the modifications thereof described above. Various changes such as combinations of the features can be made of the invention without departure of the gist of the invention. For example, if the sensors are arranged along the edge of the seated-person contact surface, the sensors 20, 22, 22R, 22F, 24, 24R, 24F, 26, 26R, 26F, 28R, 28F, 30R, 30F, 32R, 32F, 42R, 42F, 42S, 42L, and the sensor group 300 can be arbitrarily combined.

While it has been described above that the seated person assumed to have the small build is the 150-cm-tall person and the seated person assumed to have the large build is the 190-cm-tall person by way of example, the seated person of the small build and the seated person of the large build can be arbitrarily assumed. For example, in a case where only American adults are assumed to be seated or only children are assumed to be seated, the seated people are set on the basis of the physique according to the assumption. By arranging the pressure sensors along the edge of the seated-person contact surface in a state in which the seated person having the standard physique is seated, it is possible to detect the respiration signal of the seated person with high accuracy.

Moreover, it is assumed that examples of the vehicle seat include not only the vehicle seat but seats of a motorbike and a motor scooter that are land-based vehicles, and seats of a snowmobile and a personal watercraft, as well as vehicle seats of a straddle type vehicle such as a three-wheeled buggy and a vehicle seat relating to a construction machine seat.

REFERENCE NUMERALS

10 Vehicle seat
  102 Seat cushion
    102A Urethane pad
    102B Urethane slab
    102C Skin
  104 Seat back
12 Respiration measuring device
20, 22, 22R, 22F, 24, 26, 28R, 28F, 30R, 30F, 42S, 42L Sensor
24R, 26R, 32R, 42R Sensor (first sensor)
24F, 26F, 32F, 42F Sensor (second sensor)
  200, 202 Film sheet
  204 Spacer
  206, 208 Electrode
300 Sensor group
70C Arithmetic operation device
80, 80S, 80L Seated person
D Display
LA, LA1, LA2 Maximum load area

The invention claimed is:

1. A vehicle seat comprising:
a seat cushion; and
a measuring device comprising:
  at least one sensor that is provided in the seat cushion and that detects a pressure signal from a load applied from a seated person; and
  an arithmetic operation device that computes the detected pressure signal to obtain a respiration signal of the seated person, the measuring device configured to measure respiration of the seated person, wherein:
  the sensor is arranged on a back side of a back edge of a contact portion at a top portion of the seat cushion in a seated person buttocks region if a vehicle forward direction is a front direction and arranged along the back edge of the contact portion, and has a transmitter that transmits the detected pressure signal to the arithmetic operation device.

2. The vehicle seat according to claim 1, wherein the sensor has a detection surface, a lengthwise length of the detection surface being different from a crosswise length, the detection surface being arranged so that a lengthwise direction of the sensor is along the back edge.

3. The vehicle seat according to claim 1, wherein at least two sensors are provided on a front side and a back side, respectively, if a vehicle forward direction is a front direction.

4. The vehicle seat according to claim 1, wherein at least a pair of sensors are arranged to be pivoted towards an axis between the pair of sensors in a front-to-back direction if a vehicle forward direction is a front direction.

5. The vehicle seat according to claim 1, wherein the sensor has a curved shape.

6. The vehicle seat according to claim 1, wherein the sensor is provided so that at least a part of the sensor is located backward of a region where a maximum load is applied to the seat cushion from the buttocks in a state in which the seated person is seated.

7. The vehicle seat according to claim 3, wherein:
the sensor comprises a first sensor provided on the back side and a second sensor provided on the front side; and
the first sensor is arranged outward of the second sensor in a seat width direction.

8. The vehicle seat according to claim 1, wherein:
a plurality of sensors are provided as the sensor; and
the measuring device measures the respiration of the seated person by selecting data that reflects the respiration from among data detected by the plurality of sensors.

9. The vehicle seat according to claim 1, wherein the sensor is arranged to cross a centerline extending in a front-to-back direction in a region where a maximum load is applied to the seat cushion from the buttocks in a state in which the seated person is seated in a plan view.

* * * * *